(12) United States Patent
Moss et al.

(10) Patent No.: US 9,873,000 B2
(45) Date of Patent: Jan. 23, 2018

(54) LOW INTENSITY MAGNETIC FIELD DEVICES FOR TREATMENT OF CARDIAC AND NEUROLOGICAL DISORDERS

(75) Inventors: Arthur Jay Moss, Rochester, NY (US); Ilan Goldenberg, Givat Shmuel (IL); Shey-Shing Sheu, Bryn Mawr, PA (US); Gisela Beutner, Mendon, NY (US); Mark F. Bocko, Caledonia, NY (US); Ido Goldenberg, Givat Shmuel (IL)

(73) Assignee: UNIVERSITY OF ROCHESTER, Rochester, NY (US)

( * ) Notice: Subject to any disclaimer, the term of this patent is extended or adjusted under 35 U.S.C. 154(b) by 889 days.

(21) Appl. No.: 14/237,166

(22) PCT Filed: Aug. 1, 2012

(86) PCT No.: PCT/US2012/049237
§ 371 (c)(1),
(2), (4) Date: Apr. 25, 2014

(87) PCT Pub. No.: WO2013/022680
PCT Pub. Date: Feb. 14, 2013

(65) Prior Publication Data
US 2014/0228619 A1      Aug. 14, 2014

Related U.S. Application Data

(60) Provisional application No. 61/515,837, filed on Aug. 5, 2011.

(51) Int. Cl.
*A61N 2/02*       (2006.01)
*A61N 2/00*       (2006.01)
*A61N 2/06*       (2006.01)

(52) U.S. Cl.
CPC ............... *A61N 2/002* (2013.01); *A61N 2/00* (2013.01); *A61N 2/006* (2013.01); *A61N 2/02* (2013.01); *A61N 2/06* (2013.01)

(58) Field of Classification Search
CPC .................................................. A61N 2/00–2/12
USPC ....................................................... 600/13–14
See application file for complete search history.

(56) References Cited

U.S. PATENT DOCUMENTS

| 5,968,091 A | 10/1999 | Pinchuk et al. |
| 6,169,963 B1 * | 1/2001 | Markov .................. A61N 2/00 324/319 |
| 7,666,137 B2 | 2/2010 | Shallenberger |
| 2003/0158583 A1 * | 8/2003 | Burnett .............. A61N 1/36071 607/2 |

(Continued)

OTHER PUBLICATIONS

PCT International Search Report and Written Opinion for International Application No. PCT/US2012/049237; dated Oct. 9, 2012. 7 pages.

*Primary Examiner* — Catherine B Kuhlman
(74) *Attorney, Agent, or Firm* — Patent Technologies, LLC; Robert D. Gunderman, Jr.

(57) ABSTRACT

There is provided a medical device comprising a low intensity electromagnetic field source to increase the respiratory control index values (RCI) of mitochondria. The medical device may be implantable, such as a cardiac rhythm management device, a stent, or a vascular graft. The device may also be worn externally, such as a treatment device having a matrix of magnetic coils that is worn on the head for the treatment of various neurological conditions.

13 Claims, 14 Drawing Sheets

(56) References Cited

U.S. PATENT DOCUMENTS

| | | | |
|---|---|---|---|
| 2004/0181115 A1* | 9/2004 | Sandyk | A61N 1/40 600/9 |
| 2005/0148808 A1* | 7/2005 | Cameron | A61G 15/125 600/13 |
| 2007/0249911 A1 | 10/2007 | Simon | |
| 2007/0162086 A1 | 12/2007 | Dilorenzo | |
| 2009/0105779 A1 | 4/2009 | Moore et al. | |
| 2010/0057655 A1* | 3/2010 | Jacobson | A61N 2/02 706/45 |

* cited by examiner

- (X,Y) Coordinates
- Regions
- Field Strength Map
- Treatment Period
- Time Of Day For Treatment
- Frequency Of Treatment Oxygraph and Helmholtz Coils

LOW INTENSITY MAGNETIC FIELD DEVICES FOR TREATMENT OF CARDIAC AND NEUROLOGICAL DISORDERS This application claims priority to U.S. Patent Application Ser. No. 61/515,837 filed Aug. 5, 2011 entitled "Low Intensity Magnetic Field Devices For Treatment of Cardiac And Neurological Disorders" by Moss, Goldenberg, Sheu, Beutner, Bocko, and Goldenberg and to PCT International Application PCT/US2012/049237 with an international filing date of Aug. 1, 2012 entitled "Low Intensity Magnetic Field Devices For Treatment at Cardiac And Neurological Disorders" by Moss, Goldenberg, Sheu, Beutner, Bocko, and Goldenberg

TECHNICAL FIELD

The present invention relates generally to medical devices and more particularly to medical devices that generate low intensity magnetic fields for increasing respiratory control index values (RCI) as a measure of mitochondrial energy production.

BACKGROUND ART

The management and treatment of various disease conditions is an important area of medicine where much progress has taken place over the years. Oftentimes management and treatment of disease are done pharmacologically, as the administration of chemicals to the human body can often be done non-invasively, for example, orally through ingestion. The use of magnets for various purported therapeutic effects has been widely speculated and considered to be pseudoscientific since there has been a lack of quantitative scientific data to support the fact that magnets have any impact on human health or the treatment of various disease states. For example, there have been claims that magnets improve blood flow, however, scientific basis for such claims is lacking. Additionally, there have been claims that magnets reduce pain, however, such claims are again unsupported scientifically. Recent studies at the University of Rochester Medical Center, however, have determined that low intensity electromagnetic fields increase the respiratory control index values (RCI) of mitochondria, thereby improving the efficiency of this important cellular energy producing organelle without associated detrimental effects to mitochondria. Such scientific results have heretofore been unknown, the various objects of the present invention will therefore be describe herein. It is thus an object of the present invention to provide medical device that contains a low intensity electromagnetic field source. It is another object of the present invention to provide an implantable medical device that contains a low intensity electromagnetic field source. It is another object of the present invention to provide a stent for transluminal implantation that contains a low intensity electromagnetic field source. It is another objet of the present invention to provide an implantable cardiac device that contains a low intensity electromagnetic field source. It is still another object of the present invention to provide a vascular graft that contains a low intensity electromagnetic field source. It is another object of the present invention to provide a medical treatment device that is worn on the head and contains a low intensity electromagnetic field source. It is still another object of the present invention to provide a medical treatment device that is worn on the head and contains addressable sources of low intensity electromagnetic fields. These and other objects of the present invention are not to be considered comprehensive or exhaustive, but rather, exemplary of objects that may be ascertained after reading this specification and claims with the accompanying drawings.

DISCLOSURE OF THE INVENTION

In accordance with the present invention, there is provided a medical device comprising a low intensity electromagnetic field source to increase the respiratory control index values (RCI) of mitochondria.

The foregoing paragraph has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

BEST MODE FOR CARRYING OUT THE INVENTION

Studies performed and analyzed by the inventors of isolated mitochondria from the heart show that exposure to low-intensity electromagnetic fields, such as, for example, those generated by a current of 100 milliamperes through a Helmholtz coil, increase the respiratory control index values (RCI) of mitochondria, thereby improving the efficiency of this important cellular energy producing organelle. Importantly, the positive effects of exposure to low-intensity electromagnetic fields were shown to occur without associated detrimental effects to the mitochondria, and were shown to have a pre-conditioning effect. It has been shown that exposure to intermittent low-intensity electromagnetic fields results in a further increase in the efficiency of mitochondrial respiration. These effects have the potential to prolong cellular life and to prevent premature cell death (apoptosis), and can therefore be used for the management of various disease conditions, including those of the heart (for example, heart failure, prevention of progression of coronary artery disease, and healing of the heart after acute myocardial infarction) and brain (for example, traumatic brain injury, prevention of progression of Alzheimer's disease, and healing of brain cells after a cerebrovascular accident), as well as other organ systems.

In addition to the positive effects of low-intensity electromagnetic fields on mitochondria, low intensity electric fields were also shown to protect the vascular wall through endothelial dependent (increased nitric oxide production) and independent mechanisms. In addition, low intensity electric field stimulation can lead to enhanced angiogenesis through increased expression of the Vascular Endothelial Growth Factor (VEGF) protein gene.

Figure 1:
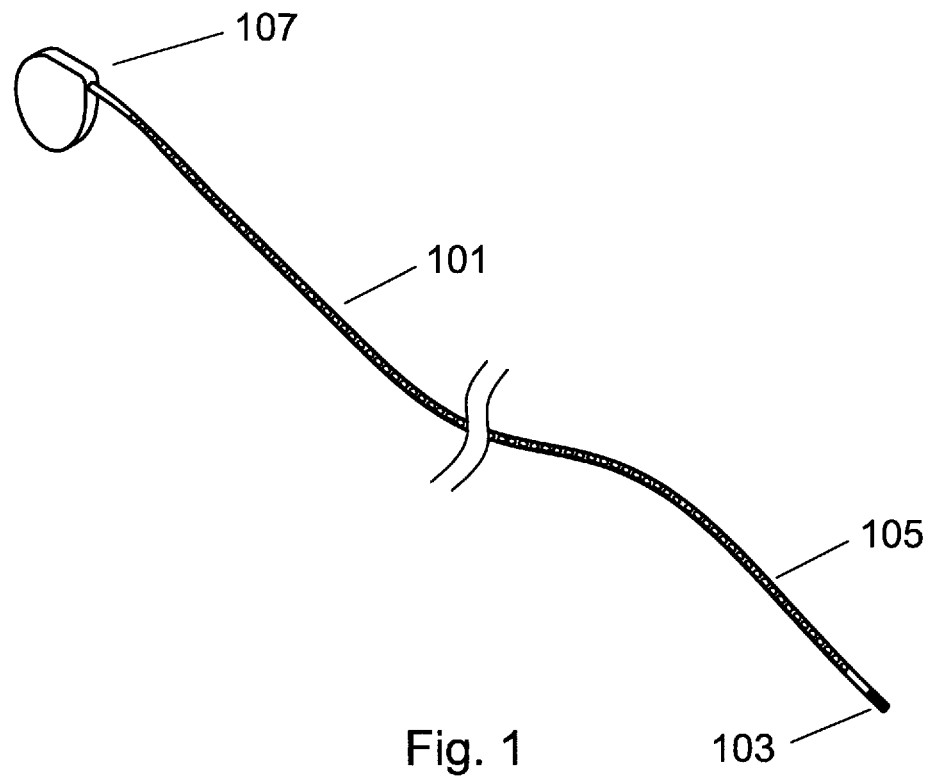
FIG. 1 depicts as cardiac rhythm management device having a lead with a low intensity electromagnetic field source.

FIG. 1 depicts a cardiac rhythm management device having a lead with a magnetic field source. The cardiac rhythm management device comprises a medical device 107 and an elongated main body lead 101. The medical device 107 comprises electronics that perform cardiac rhythm management functions that are electrically delivered to the heart by way of implantation of a metal tip 103 within a region of the myocardium. In one embodiment of the present invention, a coil or similar structure 105 is contained along at least a section of the length of the elongated main body lead 101. The coil provides a source of a magnetic field. Other embodiments of the present invention may use permanent magnet materials such as, for example, ferrite, alnico, rare earth materials, and the like. The medical device 107 contains a battery, capacitor, or other electrical charge storage device that is electrically connected to the metal tip 103 and a coil or similar structure 105. The structure may, in one embodiment of the present invention, continuously generate a low intensity magnetic field (0.01 Tesla, for example). The coil may, in one embodiment of the present invention, be a Helmholtz coil. In other embodiments, the magnetic field may be pulsed, sinusoidal, sporadic, or otherwise temporally patterned or intermittent. The magnetic field may also, in some embodiments of the present invention, change polarity, gradient, strength, polarization, direction, or other parameters.

The inventors have discovered that implantable devices that continuously generate low intensity magnetic fields may be configured to reduce the incidence of acute vascular events and the progression of atherosclerotic disease. The device of the present invention as depicted in FIG. 1 may be implanted within a region in the myocardium that is in close proximity to one or more target coronary arteries. Improved respiratory control index (RCI) values of mitochondria may be effective in treating ischemic events and improving and preserving myocardial function in heart failure patients.

Figure 2:
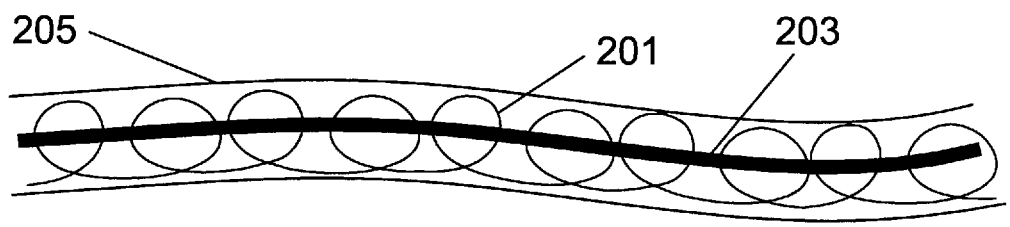
FIG. 2 depicts a lead having an electromagnetic field winding.
Figure 3:
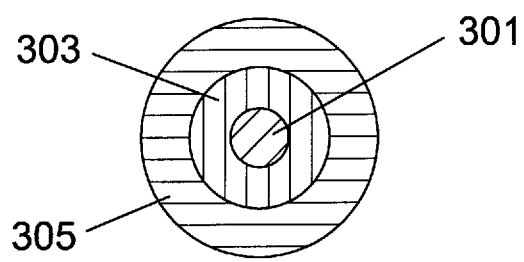
FIG. 3 is a cross sectional view of a lead having a low intensity magnetic field source layer.

In a non-limiting example, an implantable cardioverter defibrillator (ICD) is implanted in the apex of the right ventricle, in close proximity to the coronary arterial system. The implantable cardioverter defibrillator (ICD) may be configured to continuously generate a low intensity magnetic field on the order of 0.01 Tesla, for example. FIG. 2 depicts a lead having an electromagnetic field winding. The lead may be similar to that of a pacemaker lead, an implantable cardioverter defibrillator lead, or the like. A center core 203 may be a conductive core in the case of a cardiac rhythm management (pacemaker) lead or implantable cardioverter defibrillator lead. The center core 203 may also be non-conductive, or even be omitted, in some embodiments of the present invention. An electromagnetic coil 201 can also be seen encompassing the center core 203. The electromagnetic coil 201 may occupy the entire length of the lead, or may span only a portion of the length of the lead. The electromagnetic coil 201 is made from a conductive material such as, for example, copper. A biocompatible coating 205 encapsulates the electromagnetic coil 201. The biocompatible coating 205 may be, for example, a polyurethane. FIG. 3 is a cross sectional view of a lead having a low intensity magnetic field source layer. A core 301 can be seen surrounded by a magnetic field generating layer 303 that may be a conductive winding such as, for example, copper. The magnetic field generating layer may also be a permanent magnet material such as, for example, ferrite, alnico, rare earth materials, and the like. A biocompatible coating 305 encapsulates the magnetic field generating layer 303. The biocompatible coating 305 may be, for example, a polyurethane.

Figure 4:
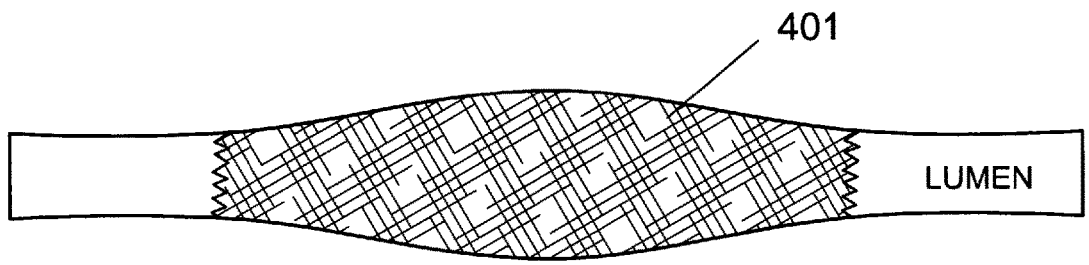
FIG. 4 depicts a stent with a low intensity electromagnetic field source coating.
Figure 5:
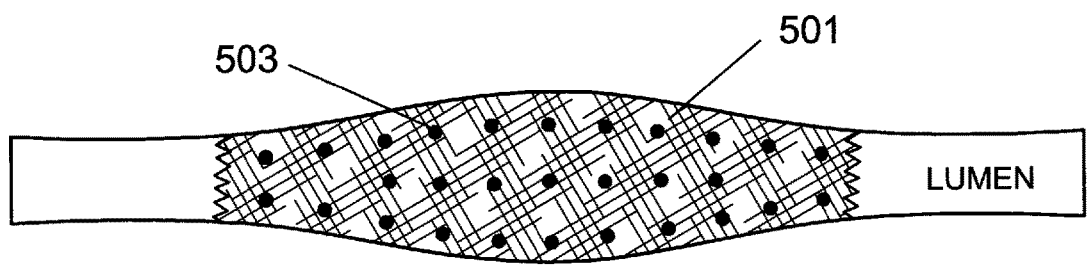
FIG. 5 depicts a stent having a plurality of low intensity electromagnetic field point sources.
Figure 6:
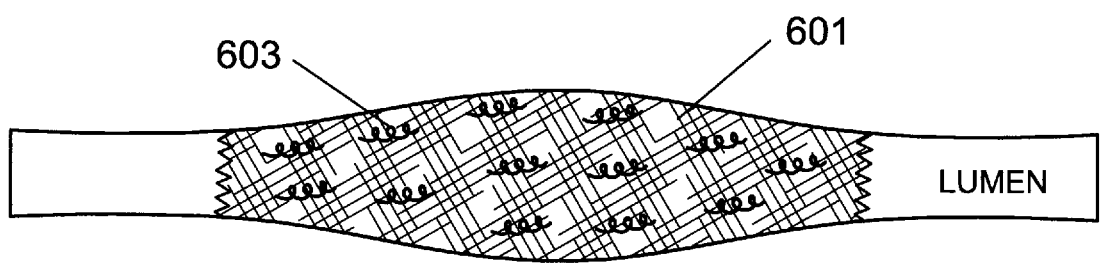
FIG. 6 depicts a stent having a plurality of electromagnetic coils.
Figure 7:
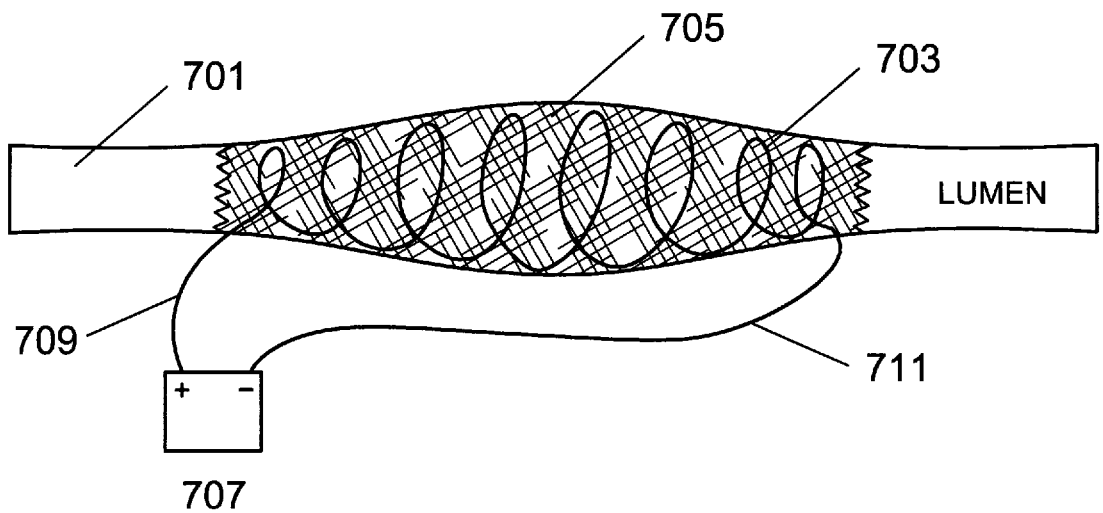
FIG. 7 depicts a stent encompassed by an electromagnetic coil.

Another application of the present invention is a stent 401, as illustrated in FIG. 4. In the stent 401 of FIG. 4, a magnetic coating or magnetic material is interspersed in the scaffold like structure of the stent. The magnetic material may be a permanent magnet material such as ferrite, alnico, rare earth materials, or the like. The magnetic material may further contain a biocompatible coating. In another embodiment of the present invention, FIG. 5 depicts a stent 501 having a plurality of low intensity electromagnetic field point sources 503. These low intensity electromagnetic field point sources 503 may be a permanent magnet material such as ferrite, alnico, rare earth materials, or the like. The magnetic material may further contain biocompatible coating. In addition to permanent magnet materials, electromagnetic coils may be used. FIG. 6 depicts a stent 601 having plurality of electromagnetic coils 603. The plurality of electromagnetic coils 603 have a source of electrical current (not shown). The electromagnetic coils are made from conductive material such as, for example, copper. FIG. 7 depicts a stent 701 encompassed by an electromagnetic coil 703. The electromagnetic coil 703 may be contained in, woven between or placed on the interior or exterior of the scaffold structure 705 of the stent. A source of electrical power 707 can also be seen attached to the electromagnetic coil 703 by way of electrical leads 709 and 711. The electromagnetic coils are made from a conductive material such as, for example, copper.

Figure 8:
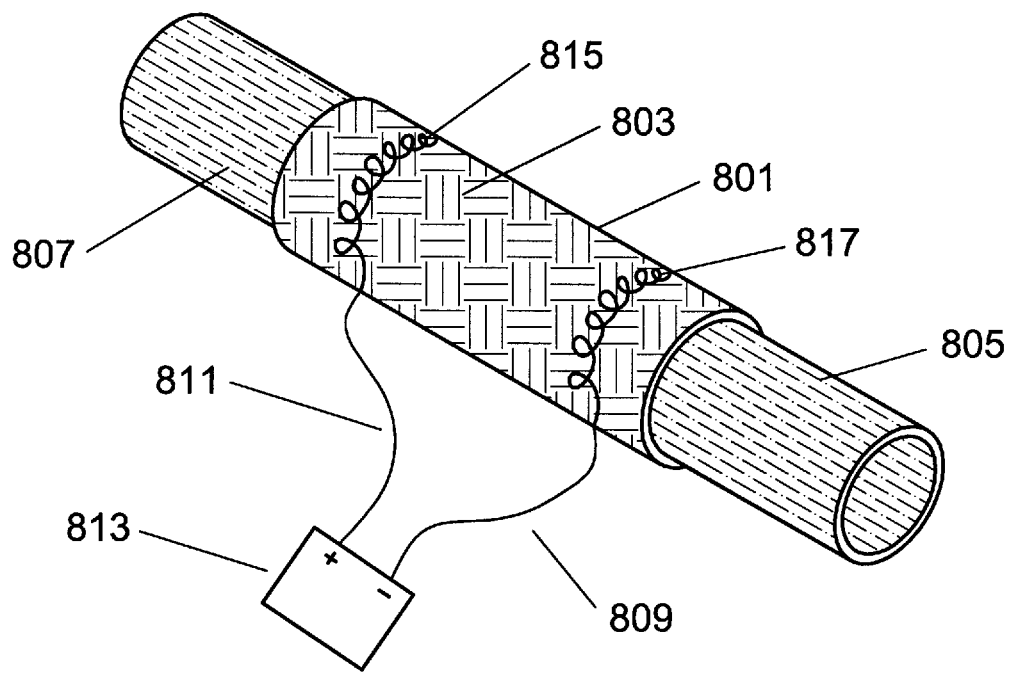
FIG. 8 depicts a vascular graft having electromagnetic coils.

Turning now to FIG. 8, a vascular graft 801 is depicted. Shown is a vessel first section 805 and a vessel second section 807. The vascular graft 801 contains a graft material 803 that is in turn wrapped otherwise surrounded by electromagnetic coils 815 and 817. The electromagnetic coils are made from a conductive material such as, for example, copper. The vascular graft 801 is implanted and the magnetic field provides therapeutic and preventive effects.

Figure 9:
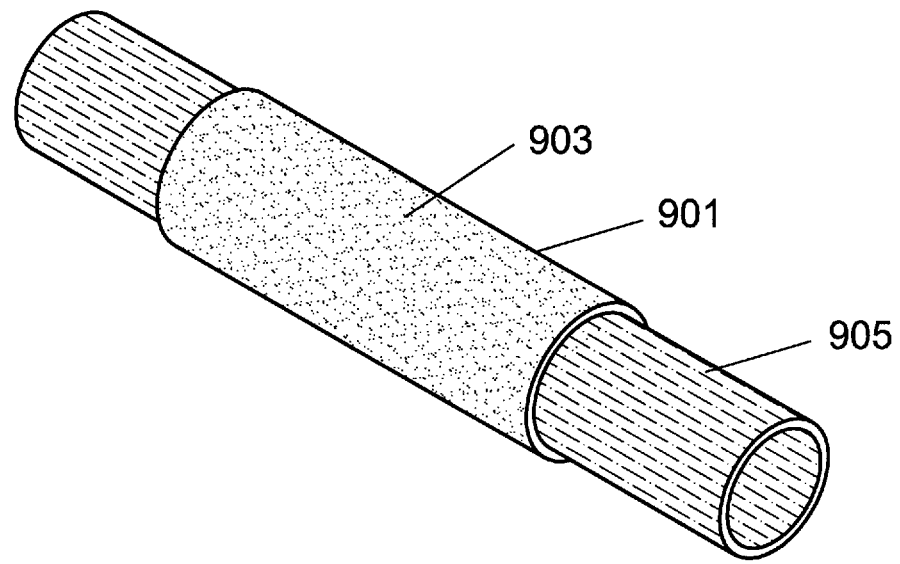
FIG. 9 depicts a vascular graft with low intensity electromagnetic field generating material.

Another embodiment of the present invention is a vascular graft with magnetic field generating material, as depicted in FIG. 9. A vascular graft 901 comprising magnetic field material 903 is depicted surrounding or otherwise replacing a diseased or damaged vessel 905. The magnetic field material may be a permanent magnet material such as a ferrite, alnico, rare earth materials, and the like.

A vascular graft may be coated or otherwise contain a magnetic field generating material. When implanted, the magnetic field generating material serves to improve respiratory control index (RCI) values of mitochondria and thus promote healing and overall graft success.

A magnetic field generating material may be disposed on the vascular graft, such as by way of a coating or covering, or the magnetic field generating material may be integral to the structure of the vascular graft and interspersed with the mechanical structure of the graft.

Figure 10:
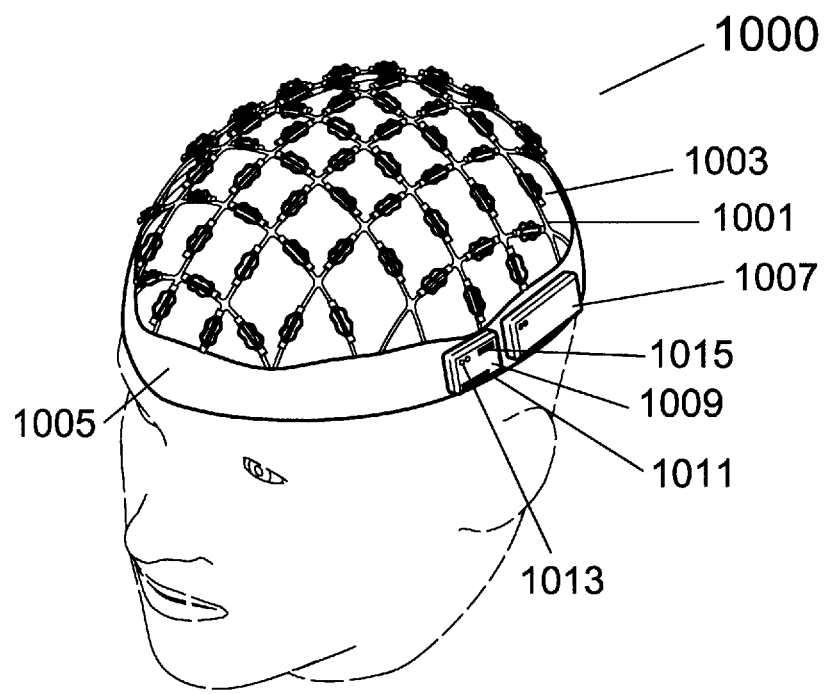
FIG. 10 is a perspective view of a low intensity electromagnetic field treatment device in use.
Figure 11:
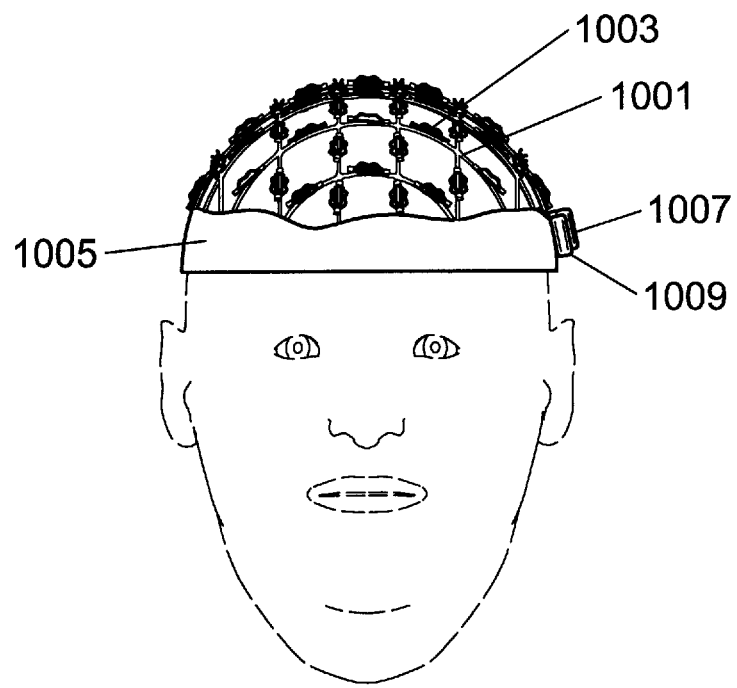
FIG. 11 is a plan view of a low intensity electromagnetic field treatment device in use.
Figure 12:
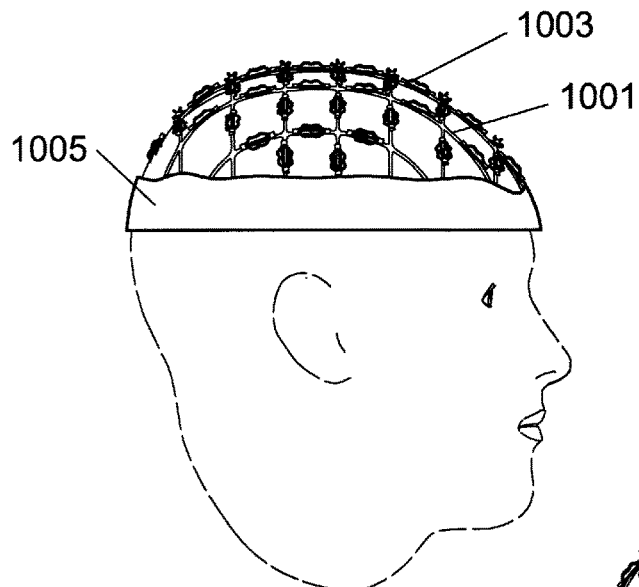
FIG. 12 is a right side view of a low intensity electromagnetic field treatment device use.
Figure 13:
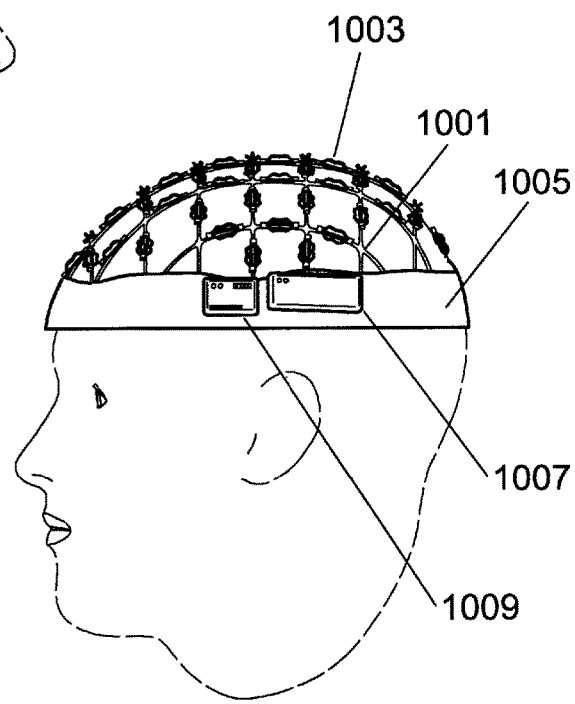
FIG. 13 is a left side view of a low intensity electromagnetic field treatment device in use.
Figure 14:
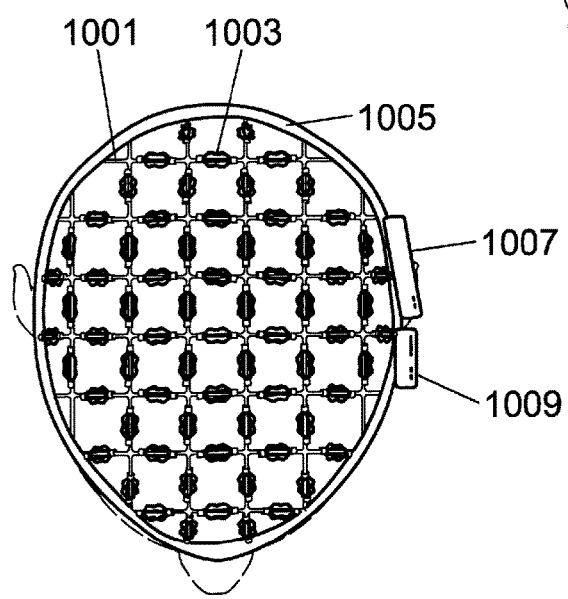
FIG. 14 is a top plan view of a low intensity electromagnetic field treatment device in use.

FIGS. 10-14 depict a low intensity electromagnetic treatment device that comprises a matrix of electromagnetic coils that are regionally addressable. The treatment device is worn on the head to treat various neurological conditions, including, for example, healing cerebrovascular events, Alzheimer's disease, and traumatic brain injury. FIG. 10 depicts a perspective view of the treatment device 1000 in use. A web or matrix 1001 can be seen that encompasses the head and is supported by a headband 1005. The web 1001 and headband 1005 may be made from a fabric such as a polyester with elastic core, a spandex material, or the like. The web 1001 supports a series of low intensity electromagnetic field coils 1003 that are electrically connected to a power source 1007 such as, for example, a rechargeable battery pack that may be, for example, a nickel metal hydride or a lithium ion rechargeable battery pack. The electromagnetic field coils are made from a conductive material such as, for example, copper. Further, a control unit 1009 is depicted that contains an electrical interface connector 1011, an on/off indicator 1013, as battery charge status indicator 1015, and other indicators and functions. To more fully describe the low intensity electromagnetic treatment device, FIG. 11 is a plan view of a low intensity electromagnetic field treatment device in use. FIG. 12 is a right side view of a low intensity electromagnetic field treatment device in use. FIG. 13 is as left side view of a low intensity electromagnetic field treatment device in use, and FIG. 14 is a top plan view of a low intensity electromagnetic field treatment device in use.

Figure 15:
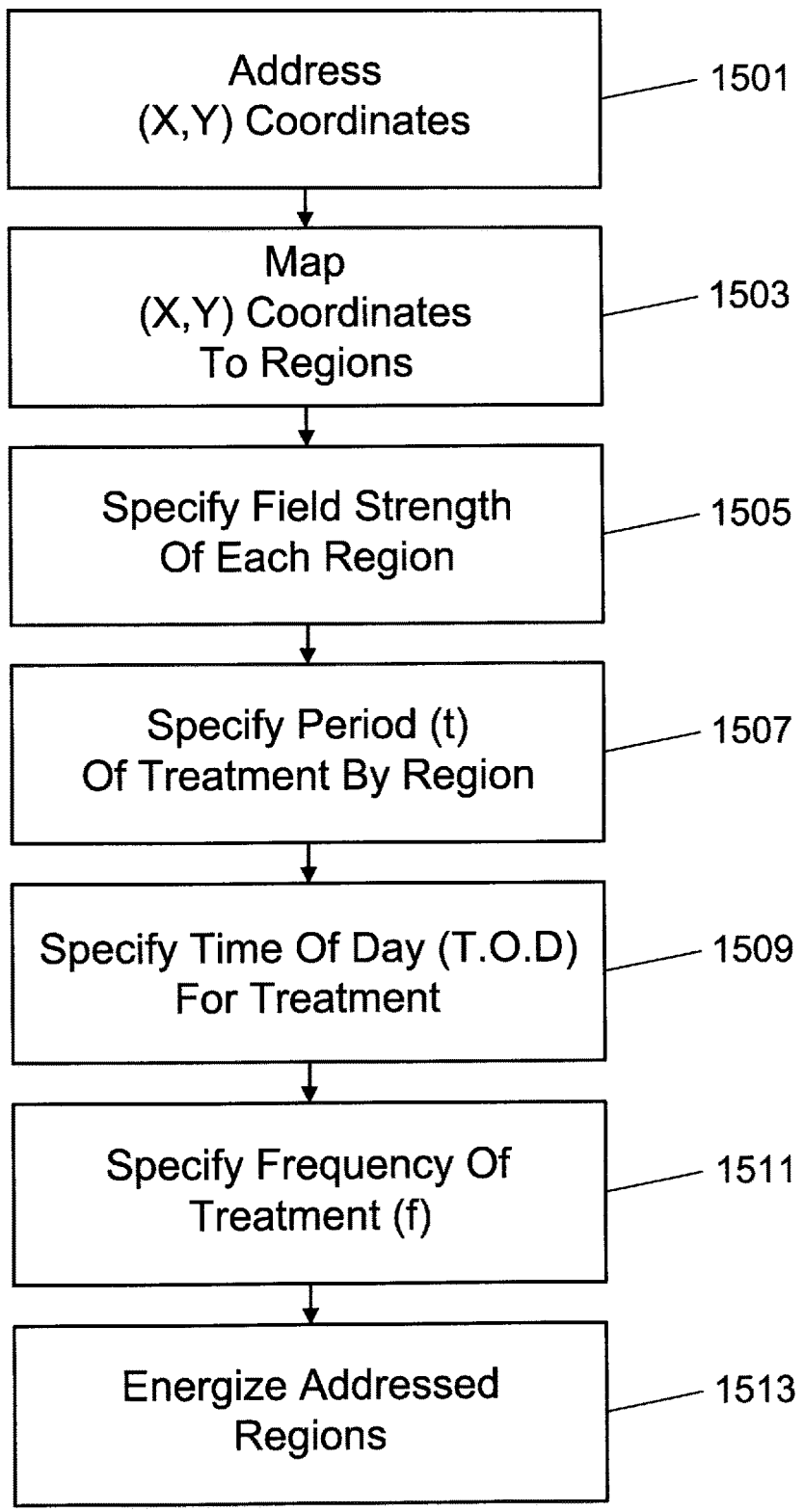
FIG. 15 is a flowchart depicting a method of operating an electromagnetic field treatment device.
Figure 17:
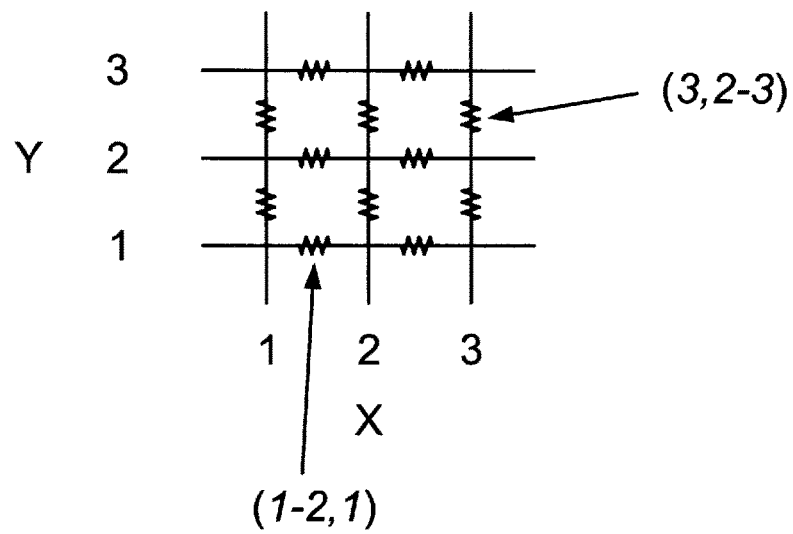
FIG. 17 is a schematic representation of an electromagnetic field treatment device matrix.

To effectively treat various neurological conditions, the treatment device contains control logic that may be implemented by way of a microprocessor and associated memory and interface circuits. The ability to address specific electromagnetic coils 1003 contained in the matrix of the treatment device provides for targeted treatment of specific regions of the head. In addition, magnetic field strength is addressable by way of a coordinate system to provide for further customized treatment. FIG. 15 is a flowchart depicting a method of operating an electromagnetic field treatment device. The various steps described relate to control functions contained within the control unit of the treatment device. Various embodiments of the treatment device may have additional steps, or less steps, than that depicted by way of FIG. 15. In step 1501, the X,Y coordinates of each coil or grouping of coils is addressed. FIG. 17 depicts a coordinate mapping system that may be used, and will be further described later in this specification. In step 1503, the X,Y coordinates are mapped to regions that may then be used to define treatment protocols. In step 1505, the magnetic field strength of each region is specified. In addition, the magnetic field strength of each coil may be specified by way of X,Y or similar coordinates. In step 1507, the period of treatment is specified by region. Step 1507 is as temporal parameter with units in seconds, minutes, hours, or days. Step 1509 specifies the time of day for treatment to be applied, and step 1511 specifies the frequency at which treatment should be applied. This may include, but is not limited to, daily, hourly, weekly, or one time. Once the various operating parameters are defined such that a treatment protocol has been defined, the addressed regions are energized with the appropriately selected magnetic field strength and operating parameters.

Figure 16:
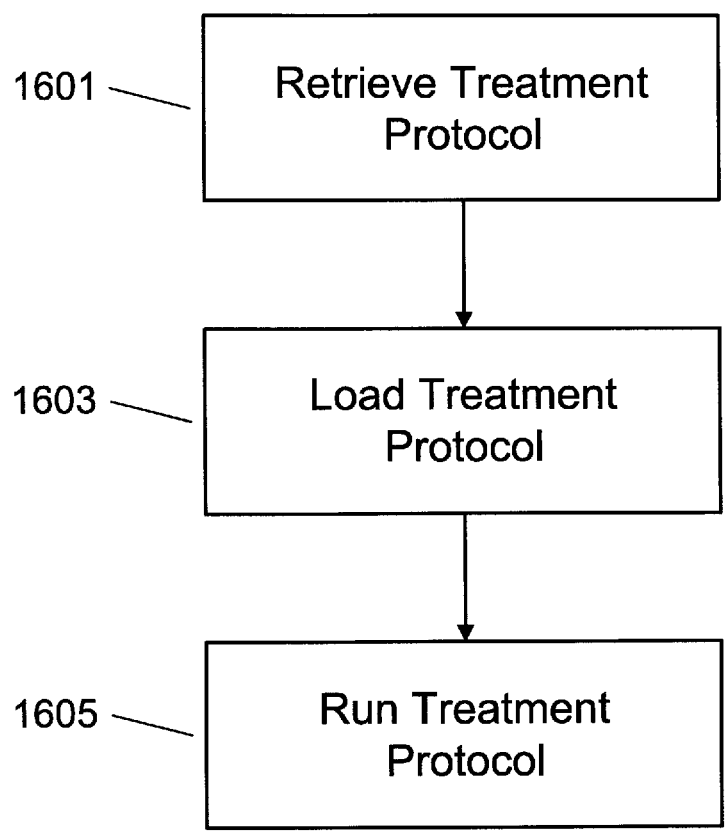
FIG. 16 is a flowchart depicting a method of use for an electromagnetic field treatment device.

FIG. 16 is a flowchart depicting a method of use for an electromagnetic field treatment device. Based on the various steps defined in FIG. 15, a treatment protocol or protocols are established. As the treatment device is used over time, a library of treatment protocols will be developed based on ongoing operating results of the treatment device. In FIG. 16, a treatment protocol is retrieved in step 1601 from a database or similar repository. In step 1603, the treatment protocol that has been retrieved is then loaded into the treatment device. In step 1605, the treatment protocol is run. A treatment protocol may contain, but is not limited to, the X,Y coordinates of the coils to be used, a definition of regions by groupings of X,Y coordinates, a magnetic field strength map, a defined treatment period, time of day for treatment, and the frequency of treatment.

FIG. 17 is a schematic representation of an electromagnetic field treatment device matrix. Such a matrix can be used to create and modify treatment protocols using the treatment device depicted in FIGS. 10-14. As can be seen in FIG. 17, a modified Cartesian coordinate system is used to address coils contained on the matrix of the treatment device. As coils span the webbing of the matrix of the treatment device, the appropriate x or y axis variable is used in conjunction with a two digit variable that represents the nodes that the coil spans. Several examples of coordinates are depicted in FIG. 17.

Figure 18:
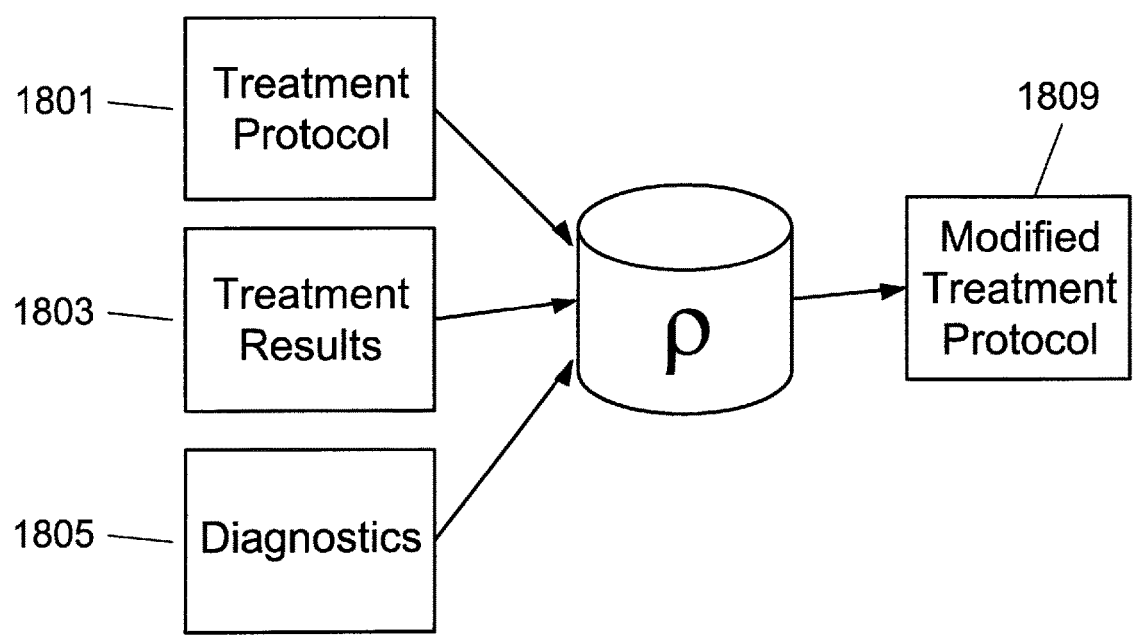
FIG. 18 is a block diagram of a process for modifying an electromagnetic field treatment device protocol.

Over time, treatment protocols will grow and be modified and improved upon. A knowledge base of treatment protocols can be collected and modified over time. Such a method is depicted by way of FIG. 18, which is a block diagram of a process for modifying an electromagnetic field treatment device protocol. Such a system for creating improved treatment protocols for the low intensity electromagnetic treatment device may, in one embodiment of the present invention, be implemented using at least one processor with access to computer readable media for retention of treatment protocols, diagnostics, and treatment results. A treatment protocol 1801 is contained in a database or similar data structure that resides computer memory, magnetic memory, optical memory, or similar computer readable media. Further, treatment results 1803 and associated diagnostics 1805 are collected and stored in a database or similar data structure that resides on computer memory, magnetic memory, optical memory, or similar computer readable media. By associating treatment results and diagnostics with treatment protocols using a processor, modified treatment protocols 1809 are produced and are also stored in a database or similar data structure that resides on computer memory, magnetic memory, optical memory, or similar computer readable media. Using this method, improved treatment protocols will be developed over time. In some embodiments of the present invention, the system for creating improved treatment protocols further comprises a network connection for retrieving treatment results, treatment protocols and diagnostics from other systems for subsequent association by the processor. Further, some embodiments of the present invention comprise a network connection for retrieving improved treatment protocols from other systems. As used in this specification, other systems refers to other computer systems, data storage systems, networks, digital devices, computers, peripherals, network elements, and the like.

The following is an experimental summary of the effects of a magnetic field on mitochondrial respiration to support the novelty of the various objects of the present invention as described and envisioned herein.

Equipment:

For the experiments performed an oxygraph with a Clark-type oxygen electrode (Hansatech, PP Systems, Amesbury Mass.) was modified. To generate a magnetic field, a pair of Helmholtz coils was mounted in the water jacket of the oxygraph chamber. The Helmholtz coils were connected to a power supply to generate magnetic fields of a defined strength. For western blotting, we used a Protean 2 electrophoresis chamber, a transfer chamber for mini gels from Biorad and an image developer from Kodak.

Methods:

Isolation of Heart Mitochondria from Mice:

Mitochondria were isolated from mouse hearts by differential centrifugation, following as published protocol (Rehncrona S, Mela L, Siesjo B K. (1979)). Recovery of brain mitochondrial function in the rat after complete and incomplete cerebral ischemia. Stroke, 10, 437-46). Briefly the heart tissue was minced in ice-cold isolation buffer (225 mM (millimolar) mannitol, 65 mM (millimolar) sucrose, 20 mM (millimolar) Tris-HCl (tris(hydroxymethyl)aminomethane) pH 7.6, 0.5 mM (millimolar) EGTA (ethylene glycol tetraacetic acid) and 0.5 mM (millimolar) EDTA (Ethylenediaminetetraacetic acid)) and then incubated with 0.005 grams of protease for 8 minutes at room temperature and gentle stirring. The protease reaction was stopped by an excess of fatty acid free bovine serum albumin and the tissue was homogenized with an Elvehjem potter (Wheaton, VWR, Radnor, Pa.). Tissue fragments, nuclei and blood cells were removed by centrifugation (1,000 g (relative centrifugal three) for 3 minutes). The mitochondria were then separated from the cytosolic compartment by centrifugation at 10,000 g (relative centrifugal force) for 10 minutes. The mitochondria containing sediment was then diluted in a small volume of EGTA (ethylene glycol tetraacetic acid) and EDTA (Ethylenediaminetetraacetic acid) free isolation buffer and kept on ice.

Oxygen Consumption:

Mitochondria (1 mg (milligram) protein) were diluted in respiration buffer (120 mM (millimolar) KCl (potassium chloride, 65 mM (millimolar) Mannitol, 35 mM (millimolar) Sucrose, 20 mM (millimolar) HEPES (4-(2-hydroxyethyl)-1-piperazineethanesulfonic acid) pH 7.2) supplemented with 2 mM (millimolar) of MgCl (magnesium chloride) and 3 mM (millimolar) of $Na_2HPO_4/NaH_2PO_4$, (disodium hydrogen phosphate/sodium dihydrogen phosphate) pH 7.4. Oxygen consumption was activated by the addition of 3 mM (millimolar) malate and 5 mM (millimolar) glutamate followed by the addition of 0.1 mM (millimolar) and 1 mM (millimolar) ADP (adenosine diphosphate).

Figure 19:
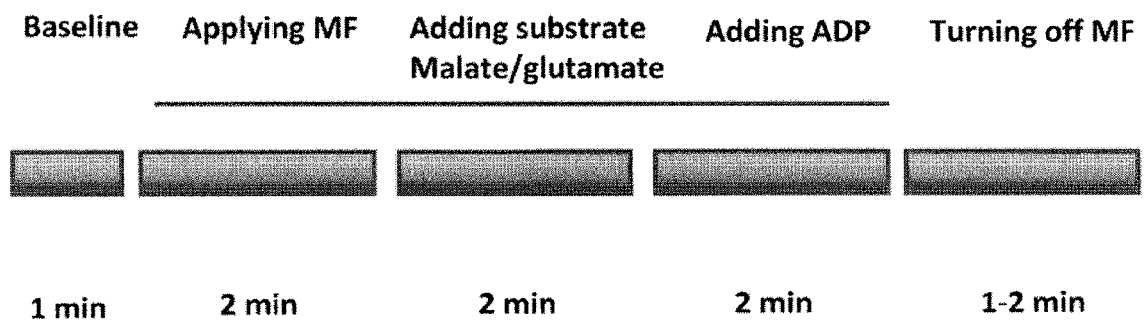
FIG. 19 depicts a timetable for conducted experiments.
Figure 19:
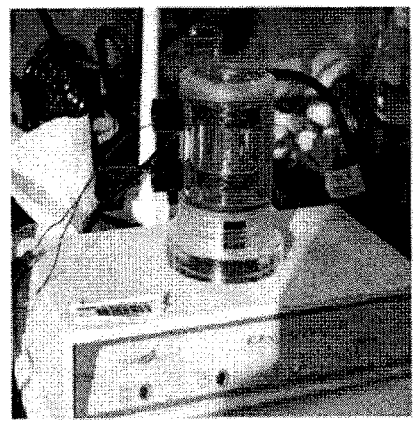

Results:

Experimental Design:

FIG. 19 shows the time frame of the performed experiments. The steps of the experiments to obtain the RCI (respiratory control index) are depicted. After obtaining as stable baseline, the magnetic field was applied to the mitochondria in the oxygraph. The red line depicted in FIG. 19 indicates the duration of the applied magnetic field. Oxygen consumption in the presence of substrate and ADP (adenosine diphosphate) was measured. Then the magnetic field was turned of and oxygen consumption was recorded for 1-2 more minutes.

Figure 20:
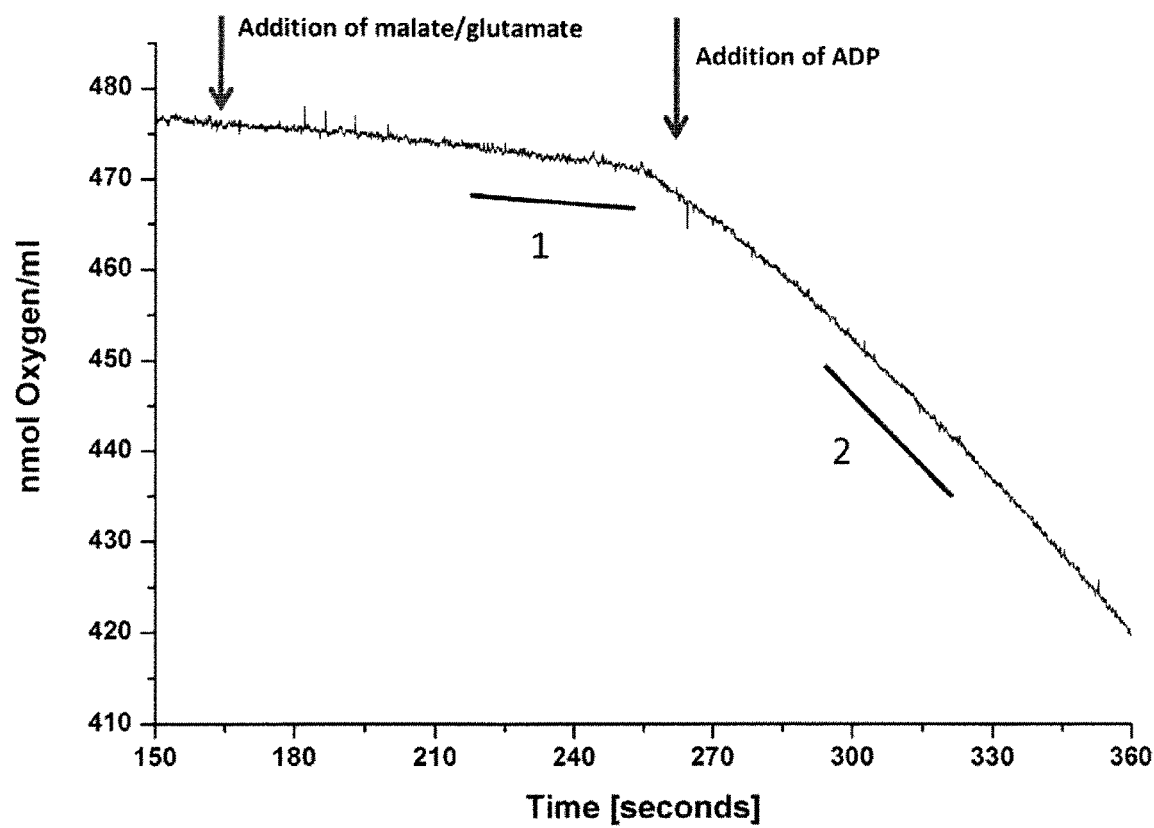
FIG. 20 is a graph of respiratory control index with no applied magnetic field.
Figure 21:
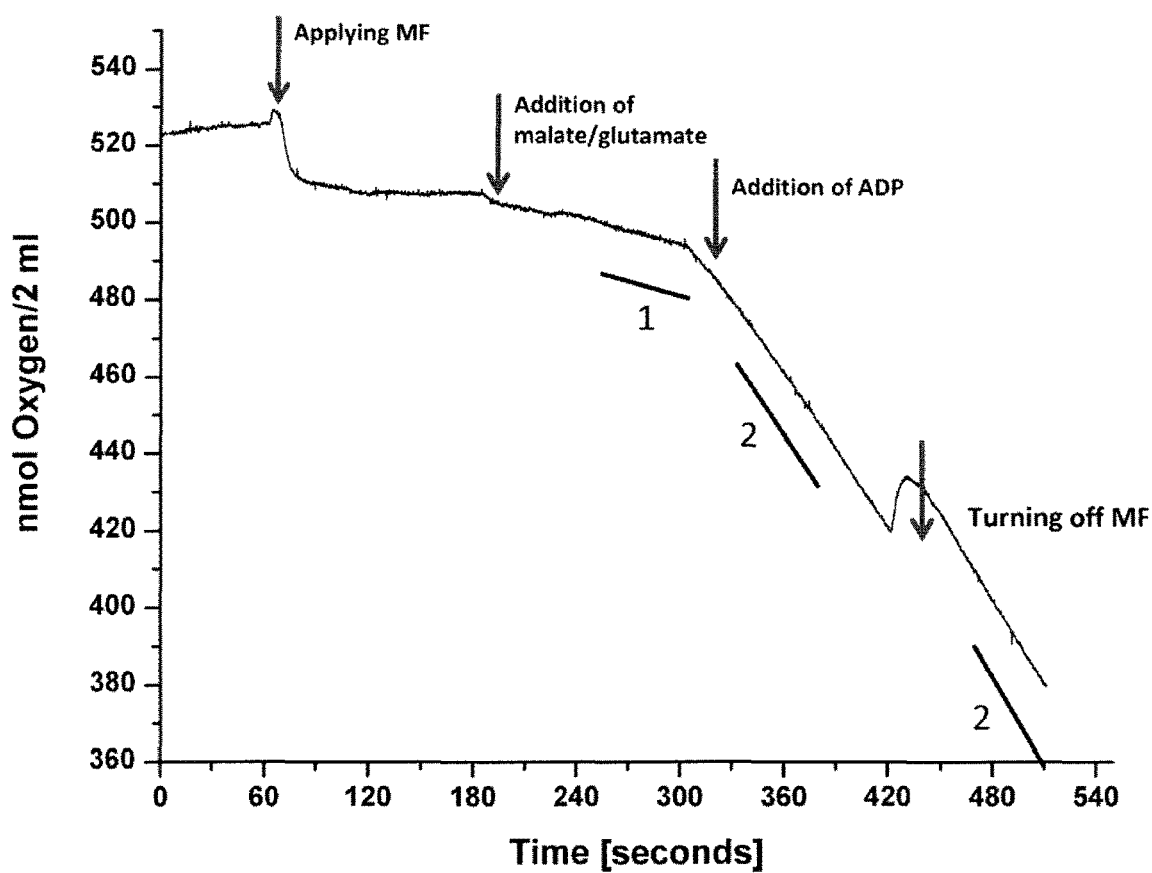
FIG. 21 is a graph of respiratory control index with an applied magnetic field.
Figure 22:
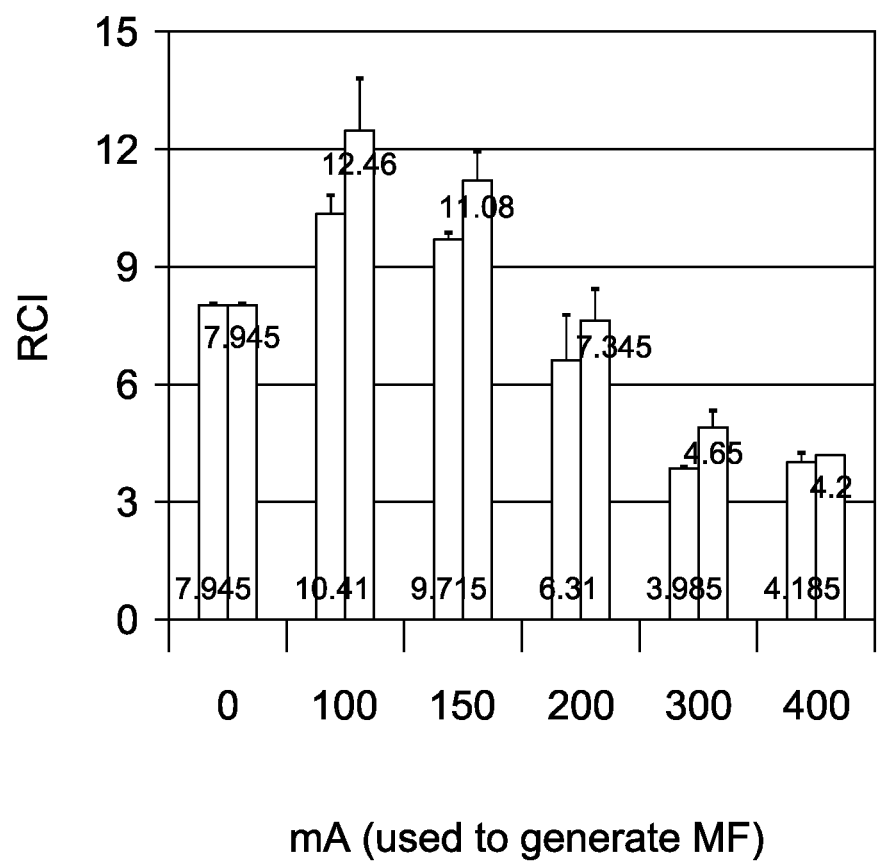
FIG. 22 is a bar graph of respiratory control index versus coil current.

Result 1. Low Magnetic Fields Improve the Respiratory Control Index (RCI):

The Respiratory Control index (RCI) indicates the ability of mitochondria to make ATP (adenosine triphosphate) by oxidative phosphorylation. Oxygen is used as a final acceptor of the electron transport chain and the usage of oxygen in the chamber of the oxygraph causes a decreasing slope (FIG. 20), which increases in the presence of a low strength magnetic field (FIG. 21). FIG. 20 depicts the resulting data with no magnetic field applied. RCI (respiratory control index) is defined as maximal oxygen consumption (slope 2) over substrate mediated oxygen consumption (slope 1). In FIG. 21, mitochondrial oxygen consumption is graphed in a magnetic field generated with 300 mA (milliamperes) of current in the experimental coil. Similar to the calculations of FIG. 20, RCI (respiratory control index) is defined as maximal oxygen consumption (slope 2) over substrate mediated oxygen consumption (slope 1). Applying a magnetic field, generated by 100 mA (milliamperes), caused an increase of the RCI (respiratory control index) from 7.945±0.037 to 10.41±0.41 (n=3, p≤0.01, t-test). Removing the magnetic field caused a further and significant increase of the RCI (respirator control index) to 12.46±1.36 (n=3, p≤0.03, t-test), suggesting an effect comparable to pre-conditioning on to the mitochondria. FIG. 22 is a bar chart depicting RCI (respiratory control index) increase with respect to applied coil current. The applied coil current is directly proportional to the magnetic field strength of the coil. The RCI (respiratory control index) improving effect was similar in the presence of a magnetic field generated by 200 mA. (milliamperes). However, stronger magnetic fields had no RCI (respiratory control index) improving effect. From the experimental results, the RCI (respiratory control index) improves the most in the presence of a magnetic field generated by a coil current of 100 milliamperes.

Figure 23:
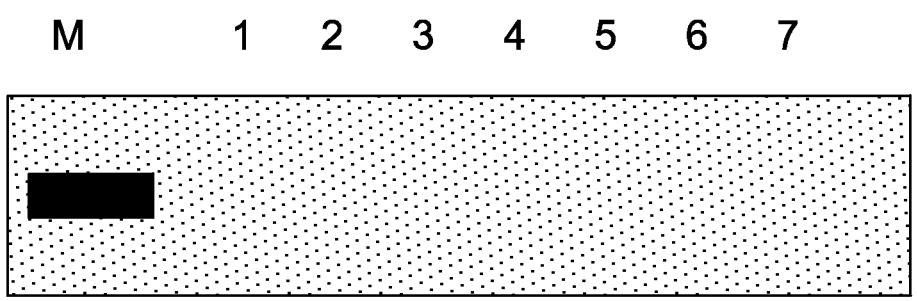
FIG. 23 depicts a representative blot of the detection of cytochrome c in the supernatant of mitochondrial samples exposed to a magnetic field.

Result 2. Low Magnetic Fields do not Cause Cytochrome c Release:

The integrity of the mitochondrial membranes is an important indication for the mitochondrial functionality. Stress for example can lead to the release of cytochrome c from the mitochondrial intermembrane space. Therefore we investigated the supernatant of each sample for the release of cytochrome c. FIG. 23 depicts a representative blot of the detection of cytochrome c in the in supernatant (lane 1-7) of mitochondrial samples exposed to a magnetic field. The strength of the field is indicated by the current (in milliamperes; mA). Where M is Mitochondria. 1: 0 mA. 2: 100 mA. 3: 200 mA. 4: 300 mA. 5: 400 mA. 6: 0 mA, 7: Control MF. Our results show that application of relatively low strength magnetic fields does not cause the release of cytochrome c in the isolated heart mitochondria (FIG. 23, lane 1-7). Even a stepwise increase of the magnetic field generated by 0 to 500 mA (milliamperes) did not cause the release of cytochrome c (lane 7).

It is, therefore, apparent that there has been provided, in accordance with the various objects of the present invention, a medical device comprising a low intensity electromagnetic field source to increase the respiratory control index values (RCI) of mitochondria.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. A low intensity electromagnetic treatment device comprising:
    a web comprising a matrix of non-overlapping low intensity electromagnetic field coils;
    a headband supporting the web for encompassing the head of a patient;
    a power source electrically connected to the matrix of low intensity electromagnetic field coils; and
    a control unit defining a coordinate system for electrically defining a location, within the matrix of low intensity electromagnetic field coils, of specific low Intensity electromagnetic field coils and comprising control logic for addressing and selectively energizing specific electromagnetic field coils to provide targeted treatment of specified regions of the head of a patient.

2. The low intensity electromagnetic treatment device of claim 1 further comprising protocols for treatment stored on computer readable media and configured to interact with the control logic of the control unit.

3. The low intensity electromagnetic treatment device of claim 2, wherein the protocols for treatment comprise a time of day parameter.

4. The low intensity electromagnetic treatment device of claim 2, wherein the protocols for treatment comprise a frequency at which treatment should be applied parameter.

5. The low intensity electromagnetic treatment device of claim 2, wherein the protocols for treatment comprise a period of treatment parameter.

6. The low intensity electromagnetic treatment device of claim 2, wherein the protocols for treatment comprise a magnetic field strength parameter.

7. The low intensity electromagnetic treatment device of claim 2, wherein the protocols for treatment comprise a magnetic field strength map parameter.

8. The low intensity electromagnetic treatment device of claim 2, wherein the protocols for treatment comprise a coil coordinate parameter.

9. The low intensity electromagnetic treatment device of claim 8, wherein coil coordinates are mapped to regions.

10. The low intensity electromagnetic treatment device of claim 2, wherein the protocols for treatment comprise a region of coil coordinates parameter.

11. A system for creating improved treatment protocols for the low intensity electromagnetic treatment device of claim 1, the system comprising:
    the low intensity electromagnetic treatment device of claim 1;
    treatment protocols for the low intensity electromagnetic treatment device of claim 8 stored on computer readable media;
    treatment results from the low intensity electromagnetic treatment device of claim 8, stored on computer readable media;
    diagnostics stored on computer readable media;
    a processor for associating the treatment results and the diagnostics with the treatment protocols to determine and provide improved treatment protocols for the low intensity electromagnetic treatment device of claim 1;
    wherein the improved treatment protocols are stored on computer readable media.

12. The system for creating improved treatment protocols of claim 11, further comprising a network connection for retrieving treatment results, treatment protocols and diagnostics from other systems for subsequent association by the processor.

13. The system for creating improved treatment protocols of claim 11, further comprising a network connection for retrieving improved treatment protocols from other systems.

* * * * *

UNITED STATES PATENT AND TRADEMARK OFFICE
CERTIFICATE OF CORRECTION

| | | |
|---|---|---|
| PATENT NO. | : 9,873,000 B2 | Page 1 of 1 |
| APPLICATION NO. | : 14/237166 | |
| DATED | : January 23, 2018 | |
| INVENTOR(S) | : Moss et al. | |

It is certified that error appears in the above-identified patent and that said Letters Patent is hereby corrected as shown below:

Column 10, Lines 23 and 24, Claim 11, 'treatment protocols for the low intensity electromagnetic treatment device of claim 8 stored on' should read -treatment protocols for the low intensity electromagnetic treatment device of claim 1 stored on- Column 10, Lines 26 and 27, Claim 11, 'treatment results from the low intensity electromagnetic treatment device of claim 8, stored on' should read -treatment results from the low intensity electromagnetic treatment device of claim 1 stored on- Signed and Sealed this
Twenty-ninth Day of May, 2018

Andrei Iancu
*Director of the United States Patent and Trademark Office*